United States Patent [19]

Bauer et al.

[11] Patent Number: 4,695,450

[45] Date of Patent: Sep. 22, 1987

[54] ANHYDROUS EMULSIONS AND THE USE THEREOF

[75] Inventors: Kurt H. Bauer, Freiburg-Tiengen; Heinrich Pins, Eberbach, both of Fed. Rep. of Germany

[73] Assignee: Warner Lambert Company, Morris Plains, N.J.

[21] Appl. No.: 540,082

[22] Filed: Oct. 7, 1983

[30] Foreign Application Priority Data

Oct. 12, 1982 [DE] Fed. Rep. of Germany ....... 3237814

[51] Int. Cl.$^4$ ...................... A61U 9/26; A61U 31/00; A61U 47/00
[52] U.S. Cl. .................................... 424/22; 514/940; 514/943
[58] Field of Search ................................ 424/168, 22

[56] References Cited

U.S. PATENT DOCUMENTS 3,169,094  2/1965  Wretlind ............................ 424/199

OTHER PUBLICATIONS

Chem. Abst. 94-1273834 (1981).
Chem. Abst. 94-7757b (1981).
Chem. Abst. 93-210271u (1980).
Chem. Abst. 10th Collective Index.
Chem. Substances Pisamin–Propanaminium 10913cs.

*Primary Examiner*—Stanley J. Friedman
*Attorney, Agent, or Firm*—Howard Olevsky; Stephen Raines

[57] ABSTRACT

Anhydrous emulsion with an oil phase (o) and a hydrophilic phase (p) of water-soluble, but anhydrous liquids, particularly as a filler matrix for medicinal preparations in capsules, which on the one hand does not attack the capsule wall and on the other permits an excellent active agent release.

6 Claims, No Drawings

ANHYDROUS EMULSIONS AND THE USE THEREOF

The present invention relates to anhydrous emulsions, which can in particular be used as basic formulations for active agents of all types which are to be encapsulated.

The liquid to pasty filling materials for capsules, particularly soft gelatin capsules, have hitherto generally been based on two types of matrixes or medicament supports, into which the active agents are incorporated prior to encapsulation. These two types are (a) oil-soluble and (b) water-soluble matrixes or medicinal vehicles.

Oil-soluble matrixes include vegetable or animal oils which, if necessary, are also combined with waxes or greases as stiffening agents or lubricants, together with mineral oils which can also contain mineral waxes or metal soaps as lubricating or stiffening agents. It is naturally also possible to encapsulate solvents, which do not attack the gelatin shell, e.g. carbon tetrachloride, ether, etc.

The water-soluble matrixes are low molecular weight polyethylene glycols or mixtures of low and high molecular weight polyethylene glycols (PEG), e.g. PEG 300 or 400 and PEG 1500, PEG 4000 or PEG 6000.

Particularly with respect to the release of the medicament, the known filler matrixes for capsules are not of an optimum nature for all active substances.

It is known that medicaments are better resorbed, if they are in dissolved form in the medicament formulations (W. A. Ritschel: Angewandte. Biopharmazie, Wiss. Verlagsgesellschaft m.b.H., Stuttgart, 1973, pp. 52 and 502). In connection with ointments it is even known that the medicinal substance dissolved in the outer or coherent phase of an emulsion is resorbed in preferred manner. Oil-soluble and water-soluble active agents are equivalently released for resorption from bicoherent, disperse systems, because both phases are cohesive (E. Nürnberg, Pharm. Zeitung, 120 (39) 1509–1519 (1975) and Deutsche Apotheker—Zeitung 117 (27), 1068–1076 (1977)).

Doubtless the same would be the case with capsule filling substances, if such emulsions were suitable for encapsulation. However, normal aqueous emulsions, no matter whether they are water-in-oil or oil-in-water emulsions, cannot be encapsulated, because the water contained therein dissolves the gelatin within a short time or at the very least attacks it strongly.

It has now been found that anhydrous emulsions consisting of an oil phase (o) and a phase (p) of water-soluble, but anhydrous liquids can be perfectly filled into gelatin capsules.

Here and hereinafter "anhydrous" is understood to mean that the hydrophilic phase (p) is in actual fact completely anhydrous or can contain up to 3% water, based on the finished capsule filling.

Preferred physiologically unobjectionable, water-soluble, but anhydrous liquids are polyethylene glycols of different molecular weights, particularly those with molecular weights between 300 and 20000, dihydric alcohols, particularly propylene glycol, or trihydric alcohols, particularly glycerol or mixtures thereof.

The hydrophilic phase can also contain further constituents, such as e.g. swelling or thickening agents, such as cellulose ester or ether, bentonites, colloidal silicon dioxide, polyacrylic acids, etc., as well as diluents, such as ethanol or other lower alcohols.

The lipophilic phase or oil phase consists of vegetable oils, e.g. groundnut oil, rape oil, animal oils, e.g. cod liver oil, halibut oil, mineral oils, e.g. paraffin oil of a highly fluid or viscous nature and/or synthetic oils, e.g. neutral oil DAC. It can also contain further constituents such as thickening agents, e.g. waxes or hydrogenated greases or oils.

It may be useful for the optimization of the bioavailability of active agents, to use further substances with a clearly defined hydrophily or lipophily and match them to one another in such a way that e.g. a desired H.L.B. value is reached. Polyhydroxyethylated oleoglycerides with different chain lengths are given as an example of this class of substances.

The emulsions can contain anionic, cationic, amphoteric and/or non-ionic emulsifiers.

It is also possible to incorporate into the emulsions antioxidants, preservatives, flavouring matter or dyes.

Precisely as in the case of conventional w/o and o/w emulsions, it has surprisingly been found that also in the case of these anhydrous emulsions, it is possible to produce propylene glycols or PEG-in-oil emulsions (p/o emulsions) and oil-in-propylene glycol or PEG emulsions (o/p emulsions), as a function of the type of emulsifiers used.

The o/p emulsions are spontaneously distributed on introducing into water or into an aqueous physiological substrate, whereas this occurs more or less slowly with p/o emulsions. These characteristics are decisive for a planned medicament release, as is shown by corresponding release tests and correspondingly also for specific activity controls.

A particular advantage compared with conventional filler matrixes is that in the case of the not infrequently encountered PEG incompatibilities, it is possible to use propylene glycol only, whilst omitting PEG. When simultaneously using oil-soluble and water-soluble active agents, it is possible to separately dissolve both medicament types and to administer them in dissolved and readily resorbable form. The hydrophilic active agent is dissolved in the propylene glycol or PEG phase and the lipophilic active agent in the oil phase. Particularly in the case of rectal and vaginal capsules it is important if the medicaments are applied in the dissolved state from the outset, because then resorption can take place more rapidly and completely.

According to the invention it is also possible to prepare emulsion types, whose melting point is above 37° C. and which are suitable for filling into hard gelatin capsules. It is known that for the filling of hard gelatin capsules with liquid or pasty substances, it is necessary to use a thixotropy process, in order to prevent the capsules from leaking. The invention makes it possible to prepare formulations where, due to their melting point, even at elevated temperatures it is possible to prevent the filled material from leaking from the hard gelatin capsules, even without thixotropy. However, after dissolving the capsules, there is a rapid disintegration of the capsule content in the stomach, because the water coming into contact therewith acts on the content in the manner of a disintegrating agent and leads to a rapid dispersion.

Retard forms can be obtained by a suitable matching of the lipophilic and hydrophilic phase, also with respect to the melting and dispersion behaviour.

The following Table shows active agent releases in vitro after 60 minutes, as a percentage of the dose used in a flow cell (artificial gastric juice: 0.1 n HCl).

Active agent release after 60 minutes as a percentage of the dose used

| Capsule filling basis | Chloramphenicol | Salicylic acid | Caffeine | Sodium salicylate |
|---|---|---|---|---|
| oil-wax* | 2.95 | 11.17 | 3.26 | 65.74 |
| PG-in-oil | 14.89 | 14.05 | 15.39 | 65.14 |
| PG-in-oil | 33.63 | 17.21 | 17.85 | 95.24 |
| oil-in-PG | 21.08 | 24.69 | 28.34 | 79.31 |

*Lipophilic standard matrix for soft gelatin capsules
PG = propyleneglycol

The following examples serve to further illustrate the invention.

EXAMPLE 1

| | | |
|---|---|---|
| p | 1,2-propyleneglycol | 100.0 g |
| | ethoxylated castor oil | 3.0 g |
| o | rape oil | 100.0 g |
| | lecithin | 1.0 g |

The ethoxylated castor oil is firstly homogenously mixed with the 1,2-propyleneglycol, (=hydrophilic phase p) and the lecithin with the rape oil (=lipophilic phase o). The two phases are then emulsified together. This gives an anhydrous o/p emulsion, which can be spontaneously dispersed extremely finely on placing in water, accompanied by gentle stirring or shaking.

EXAMPLE 2

| | | |
|---|---|---|
| p | 1,2-propyleneglycol | 2.0 kg |
| | polyoxyethylene - poly-oxypropylene polymer (PPP) | 0.02 kg |
| o | groundnut oil | 2.0 kg |
| | Glycerol monostearate | 0.01 kg |

Accompanied by heating in propylene glycol, PPP is dissolved into the water-soluble phase p and also accompanied by heating in groundnut oil, the glycerol monostearate is dissolved into the lipophilic phase o. Both phases are combined by means of suitable equipment to give a p/o emulsion.

EXAMPLE 3

| | | |
|---|---|---|
| p | Polyethylene glycol (mol. wt. 400) | 2.0 kg |
| | Cetostearyl sulphate-sodium | 0.005 kg |
| o | soy oil | 1.0 kg |
| | Cetostearyl alcohol | 0.01 kg |

The cetostearyl sulphate-sodium is dispersed in the polyethylene glycol (hydrophilic phase p). Cetostearyl alcohol is melted together with soy oil (lipophilic phase o). Both phases are then emulsified.

EXAMPLE 4

| | | |
|---|---|---|
| p | 1,2-propyleneglycol | 1.5 kg |
| | Polyethyleneglycol (mol. wt. 400) | 1.5 kg |
| | ethoxylated castor oil | 0.03 kg |
| o | soy oil | 3.0 kg |
| | lecithin | 0.09 kg |
| | chloramphenicol | 6.0 kg |

Propylene glycol, polyethylene glycol and ethoxylated castor oil as the hydrophilic phase p and vegetable oil and lecithin as the lipophilic phase o are homogeneously mixed together. Both phases are then emulsified and finally the antibiotic chloramphenicol is uniformly suspended in this emulsion and homogenized with a mill.

EXAMPLE 5

| | | |
|---|---|---|
| p | 1,2-propylene glycol | 200.0 g |
| | PPP | 0.01 g |
| | Tetracycline-HCl | 250.0 g |
| o | soy oil | 100.0 g |
| | propylene glycol monostearate | 0.02 g |
| | amphotericin B | 50.0 g |

As the hydrophilic phase p, PPP is melted in propylene glycol and the antiobiotic tetracycline-HCl is incorporated into the cooled melted substance.

As the lipophilic phase o, the propylene glycol monostearate is melted in the vegetable oil and, after cooling, the antifungal agent amphotericin B is dispersed in this phase.

Phases p and o are emulsified together and filled into the capsules in the prescribed individual dose. The aforementioned mixture gives 1000 capsules.

EXAMPLE 6

| | | |
|---|---|---|
| p | vitamin B complex | 8.0 g |
| | ascorbic acid | 50.0 g |
| | nicotinamide | 30.0 g |
| | 1,2-propylene glycol | 120.0 g |
| | ethoxylated castor oil | 1.0 g |
| o | vitamin A palmitate | 2 mill. I.U. |
| | α-tocopherol acetate | 3.0 g |
| | lecithin | 2.0 g |
| | castor oil | 120.0 g |

The water-soluble vitamins are suspended in the hydrophilic phase p and the oil-soluble vitamins are dissolved in the lipophilic phase o. The two phases are carefully emulsified and filled into 1000 capsules.

Other examples for the basic formulations are given in the following survey. The hydrophilic and lipophilic phases are prepared as described hereinbefore.

| | | 1 | 2 | 3 | 4 |
|---|---|---|---|---|---|
| p | polyethylene glycol (mol. wt. 300) | 10.0 | 10.0 | — | — |
| | 1,2-propylene glycol | — | — | 10.0 | 10.0 |
| | ethoxylated castor oil | 0.6 | 0.6 | 0.5 | 0.3 |
| | polyoxyethylene-polyoxypropylene polymer | 0.6 | 0.6 | 0.5 | — |
| | polyvinyl pyrrolidone | — | — | 1.0 | 0.5 |
| | polyacrylic acid | — | — | — | 0.5 |
| | ethanol | — | — | — | 0.5 |
| | colloidal silicon dioxide | 0.5 | 0.5 | — | — |
| | starch | — | 1.0 | — | — |
| | glycerol | — | — | 0.5 | — |
| o | vegetable oil | 10.0 | 10.0 | — | 10.0 |
| | neutral oil DAC | — | — | 10.0 | — |
| | glycerol monostearate | 0.3 | 0.3 | — | — |
| | hydrogenated soy oil | 0.3 | 0.3 | 0.3 | 0.3 |

|   | 1 | 2 | 3 | 4 |
|---|---|---|---|---|
| polyethylene glycol-400-monostearate | — | — | 0.3 | 0.3 |

In a further survey, a number of formulations are given for the active agent caffeine which, in the case of an identical agent content, differ with regards to their consistency and their dispersibility in water. During preparation, the active agent can be finely dispersed in one phase prior to the emulsification of both phases, or can be finely dispersed in the emulsion following the emulsification of the phases.

|   |   | 1 | 2 | 3 |
|---|---|---|---|---|
| p | 1,2-propylene glycol | 45.5 | 42.0 | 44.0 |
|   | hydroxypropyl-cellulose | 3.0 | 3.0 | 3.0 |
|   | ethoxylated castor oil | 1.5 | — | 1.5 |
|   | polyoxyethylene-polyoxypropylene polymer | — | 5.0 | 1.5 |
|   | caffeine | 50.0 | 50.0 | 50.0 |
| o | vegetable oil | 42.0 | — | 42.0 |
|   | neutral oil DAC | — | 40.0 | — |
|   | lecithin | 0.5 | — | 1.0 |
|   | hydrogenated soy oil | 7.5 | 7.5 | 7.0 |
|   | glycerol monostearate | — | 2.5 | — |

We claim:
1. An anhydrous physiologically acceptable carrier comprising an emulsion of (1) a hydrophobic liquid selected from the group consisting of a vegetable oil, an animal oil, a mineral oil, a synthetic oil and mixtures thereof and (2) a hydrophilic, anhydrous liquid.
2. A carrier according to claim 1 wherein the hydrophilic liquid is selected from the group consisting of polyethylene glycol, lower aliphatic polyhydric polyols and mixtures thereof.
3. A medicinal dosage for a medicament comprising a gelatin capsule and an anhydrous, physiologically acceptable, emulsified carrier contains a hydrophilic phase selected from the group consisting of polyethylene glycol, lower aliphatic polyhydric alcohols and mixtures thereof, wherein the carrier contains an oil phase selected from the group consisting of a vegetable oil, an animal oil, a mineral oil, a synthetic oil and mixtures thereof.
4. The dosage according to claim 3 wherein the medicament is hydrophobic and is dissolved in the oil phase.
5. A dosage according to claim 2 wherein a hydrophobic medicament is dissolved in the oil phase and a hydrophilic medicament is dissolved in the hydrophic phase.
6. A dosage according to claim 2 wherein a hydrophilic medicament is dissolved in the hydrophilic phase.

* * * * *